United States Patent [19]

Langer et al.

[11] Patent Number: 4,567,883
[45] Date of Patent: Feb. 4, 1986

[54] DATA COMPRESSION OF ECG DATA USING DELTA MODULATION

[75] Inventors: Alois A. Langer; Mir Imran, both of Pittsburgh, Pa.

[73] Assignee: Mieczyslaw Mirowski, Owings Mills, Md.

[21] Appl. No.: 502,499

[22] Filed: Jun. 9, 1983

[51] Int. Cl.[4] ............................................... A61B 5/04
[52] U.S. Cl. ............................. 128/696; 128/419 PT; 375/28
[58] Field of Search ............... 128/695, 696, 710, 903, 128/419 D, 419 PG, 419 PS, 419 PT; 375/28–33

[56] References Cited

U.S. PATENT DOCUMENTS

| | | | |
|---|---|---|---|
| 3,603,881 | 9/1971 | Thornton | 128/903 |
| 3,815,033 | 6/1974 | Tewksbury | 375/32 |
| 4,027,266 | 5/1977 | Clark | 375/28 |
| 4,041,954 | 8/1977 | O'Hara | 128/697 |
| 4,042,921 | 8/1977 | Smith | 375/30 |
| 4,223,678 | 9/1980 | Langer et al. | 128/419 D |
| 4,295,474 | 10/1981 | Fischell . | |

OTHER PUBLICATIONS

All-Digital Continuously Variable Slope Delta Modulator (CVSD) Harris Corporation, 1977.

Primary Examiner—William E. Kamm
Attorney, Agent, or Firm—Fleit, Jacobson, Cohn & Price

[57] ABSTRACT

A data recording arrangement for recording ECG data within the body of a patient, for transmitting the ECG data to a point external to the body of a patient, and for recovering the transmitted ECG data is disclosed. The recording arrangement employs delta modulation circuitry for delta modulating the ECG data to obtain a delta modulated digital pulse train. The digital pulse train may be stored within the body of a patient for subsequent transmission external to the body of a patient. Transmission of the data external to the body of a patient may be by a piezoelectric transducer which transmits the digital data audibly for external detection and delta demodulation. Alternatively, delta demodulation may occur within the patient's body, and the demodulated analog signal may then be transmitted by FM, using the piezoelectric transducer to provide the FM audible signal detectable by an FM demodulator external to the body.

24 Claims, 6 Drawing Figures

DATA COMPRESSION OF ECG DATA USING DELTA MODULATION

BACKGROUND OF THE INVENTION

1. Field of the Invention

The present invention relates to the data compression of ECG data using delta modulation, and more particularly to an arrangement for recording ECG data in accordance with data compression utilizing a delta modulation technique.

2. Description of the Prior Art

Recent efforts in the area of cardiac technology have been directed toward the development of techniques and devices for recording ECG data derived via electrodes connected to the heart of a subject. One prior art technique or arrangement calls for the electrodes to be affixed to the patient in proximity to the heart for the development of ECG data, but such an arrangement and technique calls for the subject to be permanently connected to the recording unit. As a result, ECG data can only, as a practical matter, be developed over a relatively short period of time.

A further arrangement of the prior art is disclosed in U.S. Pat. No. 4,223,678—Langer et al, issued on Sept. 23, 1980. That patent discloses a device for recording and subsequently reproducing information, such as desired portions of an ECG signal produced by a heart, prior to and during the occurrence of a disturbance in cardiac electrical activity. Two basic embodiments of the recorder are shown: one embodiment is fully implantable and is encased within sensing and defibrillating electronics, and includes a continually updated recorder and a high-capacity stand-by recorder actuated upon the sensing of fibrillation, with the recorded information being retrieved by telemetry using an external device; the second embodiment comprises an external device having external electrodes, with the ECG information being transmitted to the recorder unit by telemetry. Reference should also be made to U.S. Pat. No. 4,295,474—Fischell, issued on Oct. 20, 1981, which shows an ECG recorder.

It should be appreciated that the above arrangements for recording ECG information are limited by the storage capacity of the recording unit. The present invention provides for a more efficient use of the limited storage capacity by employing a delta modulation data compression technique, in particular, a continuously variable slope delta modulation technique. Continuously variable slope delta modulators (CVSD) have been used, particularly in voice transmission, as described in a 1977 copyrighted publication by Harris Semiconductor, HC-55516/55532, "All-Digital Continuously Variable Slope Delta Modulator (CVSD)" and Harris Semiconductor, Application Note 607, "Delta Modulation for Voice Transmission", January, 1979.

In various prior art arrangements, such as that disclosed in the aforementioned Langer et al patent, the recording of cardiac data by fully implanted devices has necessitated the retrieval of that data by means of transmission through the skin of the subject by such means as induction coupling. Techniques such as induction coupling are characterized by disadvantages which are well known to those of skill in the art. Thus, the present invention is also directed to overcoming these disadvantages.

More specifically, the present invention employs a piezoelectric transducer technique which, besides being simpler than the induction coupling technique, permits the user to aurally monitor the heart beat.

SUMMARY OF THE INVENTION

According to the present invention, there is provided a recording unit for recording ECG data utilizing data compression in accordance with a delta modulation technique.

Specifically, the invention is directed to the provision of a recording unit which can, if desired, be fully implanted within the body of a subject, and which is connected, via electrodes and conventional ECG amplifier circuitry, to the heart of the subject for deriving ECG data therefrom. The recording unit is preferably actuated by the detection of an arrythmia, and the derived data is, in accordance with the data compression (delta modulation) technique, stored within the recording unit in digital form. The digital data thus stored may be subsequently retrieved by transmission, via a piezoelectric transducer, through the skin of the subject to a conventional pickup (such as a microphone). Such data transmission can occur in two ways. First, the compressed data can be transmitted digitally to an external delta demodulator which receives the digital data and demodulates such data in accordance with a delta demodulation technique to reconstruct the ECG waveform in analog form. Second, the compressed data can be demodulated within the implanted device to reconstruct the ECG waveform in analog form and then the analog ECG waveform is transmitted to an external receiver. The latter transmission could occur by an AF oscillator which excites the piezoelectric transducer in accordance with FM techniques.

Therefore, it is an object of the present invention to provide a recording unit for recording ECG data utilizing data compression in accordance with a delta modulation technique, particularly a continuously variable slope delta modulation technique.

It is an additional object of the present invention to provide a recording unit which may be fully implanted within the body of a subject.

It is an additional object of the invention to provide a recording unit which is actuated by detection of fibrillation or tachycardia.

It is an additional object of the present invention to provide a data recording unit which, as a result of its operation in accordance with the delta modulation technique, is capable of recording large amounts of ECG data over an extended period of time.

It is an additional object of the present invention to provide a recording unit from which data can be retrieved by means of transmission through the skin of the subject via piezoelectric transducer circuitry.

It is an additional object of the present invention to provide a recording arrangement wherein delta demodulation circuitry is employed, external to the subject, for demodulating the data transmitted from the fully implanted data recorder.

The above and other objects that will hereinafter appear, and the nature of the invention, will be more clearly understood by reference to the following description, the appended claims, and the accompanying drawings.

DETAILED DESCRIPTION

The present invention will now be more fully described with reference to FIG. 1, which is a schematic diagram of the recording unit of the present invention.

Figure 1:
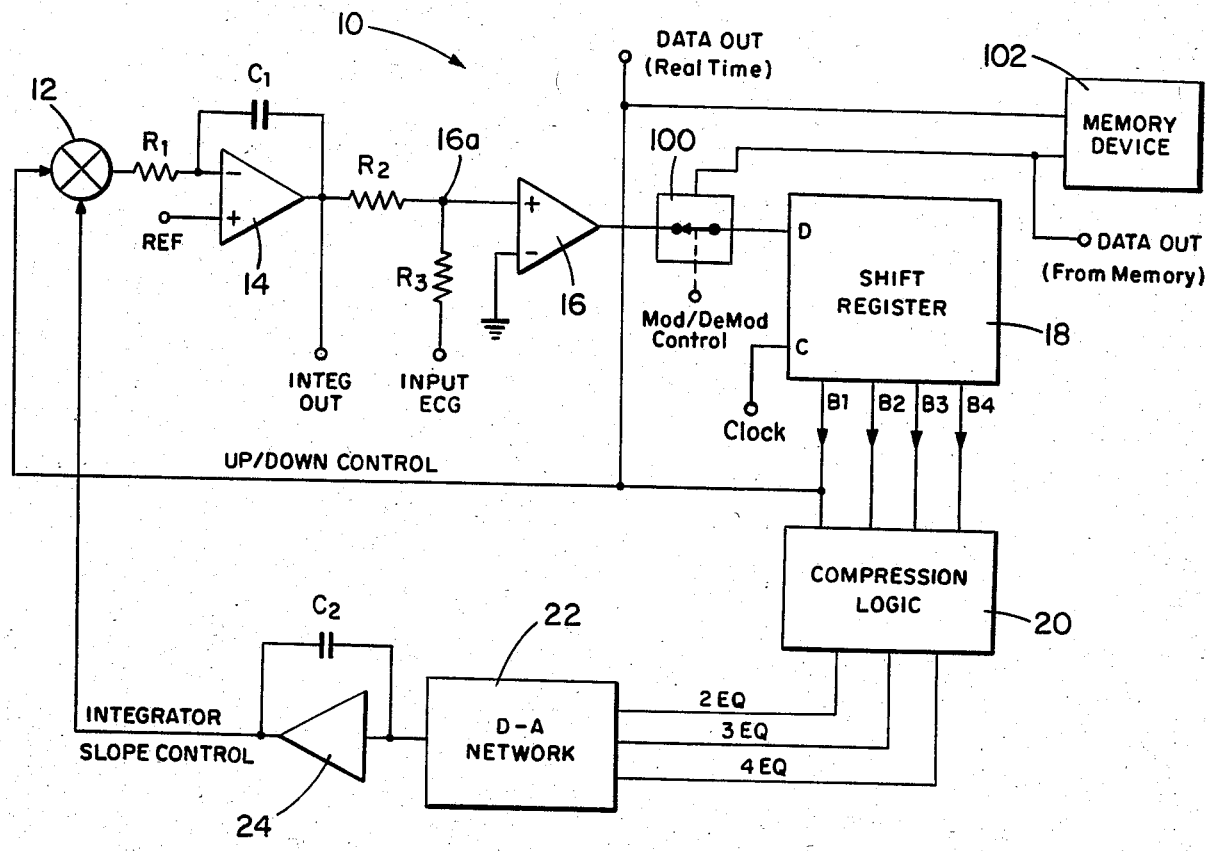
FIG. 1 is a schematic diagram of the data recorder of the present invention.

Referring to FIG. 1, the recording unit 10 of the present invention generally comprises multiplier 12, integrator 14, comparator 16, shift register 18, compression logic 20, D-A network 22, and integrator 24, as well as a modulate/demodulate control switch 100 and memory device 102.

In operation, the recording unit 10 may be automatically actuated by detection of an arrythmia by any suitable arrythmia detector (not shown). When the recording unit is actuated, ECG data is provided to the recorder via terminal INPUT ECG, and is provided via resistor R3 to the junction 16a connected to the positive terminal of comparator 16. Junction 16a is also connected via resistor R2 to the output of integrator 14, the integrator 14 integrating in the upward or downward direction as a result of a control signal (UP/DOWN CONTROL) provided to one input of multiplier 12 from the output B1 of shift register 18.

Thus, during each clock period, integrator 14 integrates in the upward or downward direction in accordance with the control signal from output B1, with the integrator output being provided via resistor R2 to the terminal 16a. The positive terminal of comparator 16 is connected to terminal 16a such that comparator 16 issues a first binary output when the output of integrator 14 is greater than the ECG input (binary "1"), and issues another binary output when the output of integrator 14 is less than the ECG input (binary "0"). When the control switch 100 is in the modulate mode, as shown in FIG. 1, the binary output of comparator 16 is shifted into shift register 18 by means of its D input.

Shift register 18 comprises, in this embodiment, a four-stage binary shift register, with the first stage of the shift register providing a binary output (via terminal B1) both to the memory device 102 of the recorder 10 and to the UP/DOWN CONTROL input of multiplier 12. The memory device 102 may be any suitable storage device, such as a silicon memory chip. The memory device 102 stores the binary data, representative of delta modulated compressed ECG data, for subsequent transmission external to the patient in a manner to be described. Similarly, the data from terminal B1 may be transmitted in real time via the DATA OUT (REAL TIME) terminal.

The recorder 10 employs a continuously variable slope delta modulation technique by virtue of the fact that (1) the binary output of shift register 18 is fed back to one input of multiplier 12 and then to integrator 14, and (2) the binary contents of shift register 18 are utilized (in a manner now to be described) to control the integrator 14 slope via the INTEGRATOR SLOPE CONTROL input of multiplier 12.

To further describe the operation of the data recorder 10, if, at an arbitrary commencement of operation, the signal at junction 16a is positive (indicating that the output of integrator 14 exceeds the ECG input), the output of comparator 16 is positive, and the shift register 18 receives binary "1" inputs, which are clocked into the shift register by a clock signal at terminal C of the shift register. The data output (from B1) of shift register 18 is accordingly binary "1" outputs, and these provide the control input to multiplier 12, resulting in integration in the downward direction (UP=0, DOWN=1). If comparator 16 issues two identical binary outputs in sequence, this results in identical binary outputs B1 and B2 from shift register 18 to compression logic 20, and compression logic 20 activates the 2EQ output to D-A network 22. D-A network 22 causes integrator 24 to commence integration, thus controlling the integration slope via the control input to multiplier 12. As a result of change of the slope of integration, the next integration step within a time period becomes larger than the previous one. In essence, the time constant of integrator 14 is altered by the integrator slope control signal so as to follow the input ECG.

Normally, an integrator has a maximum slope, and therefore it sometimes cannot keep up with the waveform being "tracked". However, ideally, the integrator should be set at maximum slope so as to be able to "track" the waveform (the input ECG waveform). In fact, as will be seen below, with reference to the detailed description of compression logic 20 and D-A network 22, the recorder of the present invention is able to achieve superior results in "tracking" the ECG waveform.

More specifically, as will be described in more detail below, compression logic 20 contains logic circuitry such that output 2EQ is activated when bits B1 and B2 are identical, output 3EQ is activated when bits B1, B2 and B3 are identical, and output 4EQ is activated when bits B1, B2, B3 and B4 are identical. As soon as the first two bits are identical, the output 2EQ is provided, via D-A network 22 (which converts the binary input to an analog output), as an input to the integrator 24, by means of which integration slope is controlled via the INTEGRATOR SLOPE CONTROL input to multiplier 12. Thus, integrator 24 changes the slope of integration of integrator 14. The network 22 can, in accordance with the present invention, be any network for changing the integration slope in a linear or non-linear (for example, logarithmic) fashion so as to permit faster upward or downward change of slope of the recorded ECG signal.

Figure 2:
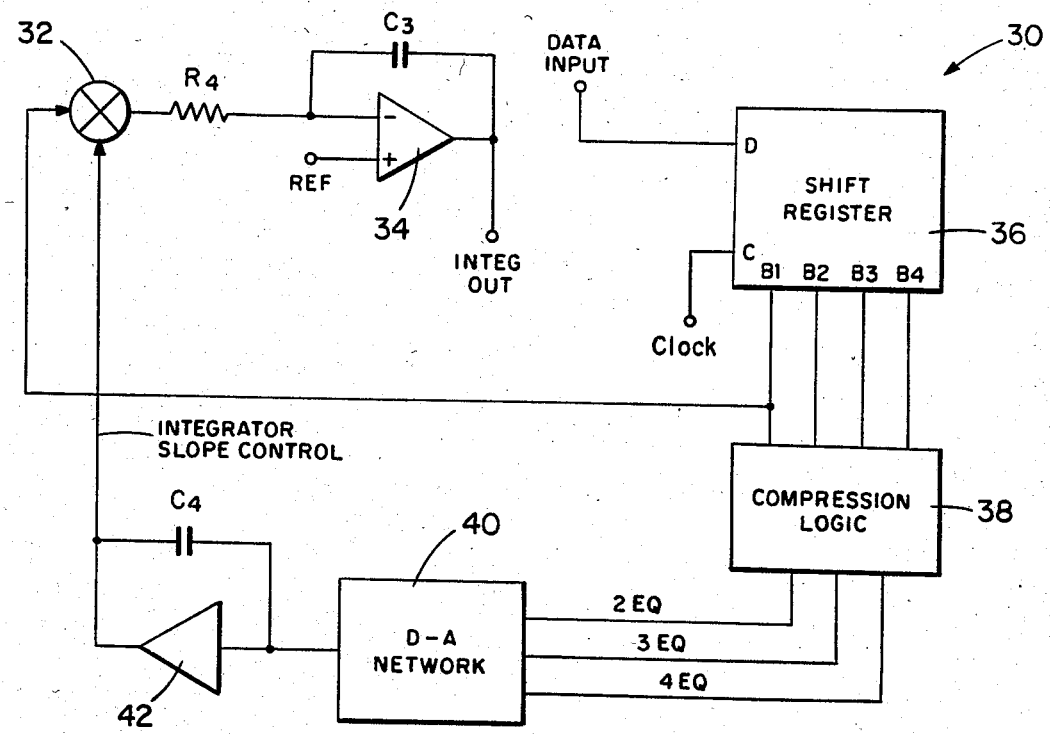
FIG. 2 is a schematic diagram of external demodulation circuitry for demodulating data retrieved from the recorder of FIG. 1.

FIG. 2 is a schematic diagram of external demodulation circuitry to be employed for demodulating the digital data transmitted externally, such digital data being that stored in the memory device 102 (via DATA OUT—From Memory terminal) or that transmitted in real time. As seen in FIG. 2, the demodulation circuitry 30 includes multiplier 32, integrator 34, shift register 36, compression logic 38, D-A network 40 and integrator 42. Thus, it is evident that the demodulation circuitry 30 of FIG. 2 corresponds substantially to the recorder circuitry of FIG. 1, except that the comparator 16, associated junction 16a, resistors R2 and R3, INPUT ECG terminal, MOD/DEMOD control switch 100, and memory device 102 have been eliminated. The DATA INPUT terminal of the demodulator 30 receives the transmitted digital signals (transmitted in a manner to be described below) and shifts the input into the shift register 36 in accordance with a clock signal applied to the CLOCK input, terminal C, of the shift register 36. The demodulator 30 demodulates the digital input signals into an analog signal, at INTEG OUT terminal of integrator 34, to reconstruct the ECG signal. The various components of the demodulator 30 operate in an analogous manner to that of FIG. 1.

Figure 3:
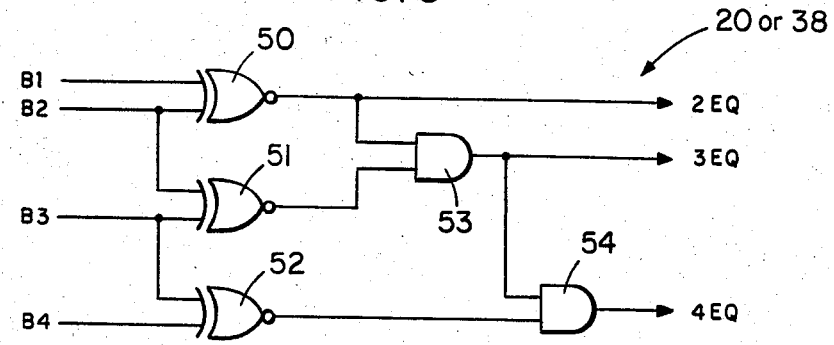
FIG. 3 is a logic diagram of the compression logic of the recorder and demodulation circuitry of FIGS. 1 and 2, respectively.

FIG. 3 is a detailed schematic of the compression logic 20 and 38 of FIGS. 1 and 2, respectively, and comprises NOR gates 50-52 and AND gates 53 and 54. In operation, compression logic 20 and 38 provide a positive 2EQ output when binary inputs B1 and B2 are identical, provides a positive 3EQ output when binary inputs B1, B2 and B3 are identical, and provides a positive 4EQ output when binary inputs B1–B4 are all identical.

Figure 4:
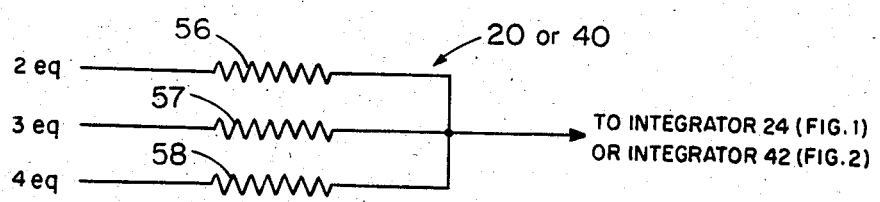
FIG. 4 is a schematic diagram of the digital-to-analog (D-A) network of the recorder and demodulation circuitry of FIGS. 1 and 2, respectively.

FIG. 4 is a detailed schematic of the D-A networks 22 and 40 of FIGS. 1 and 2, respectively, and includes resistors 56, 57 and 58. The resistance of resistors 56, 57 and 58 are appropriately chosen (for example, 1.2 megohms, 3.3 megohms and 4.7 megohms, respectively), such that the input to integrator 24 (FIG. 1) or integrator 42 (FIG. 2) is appropriately controlled and responds to activation of corresponding binary inputs 2EQ, 3EQ and 4EQ, respectively.

Figure 6:
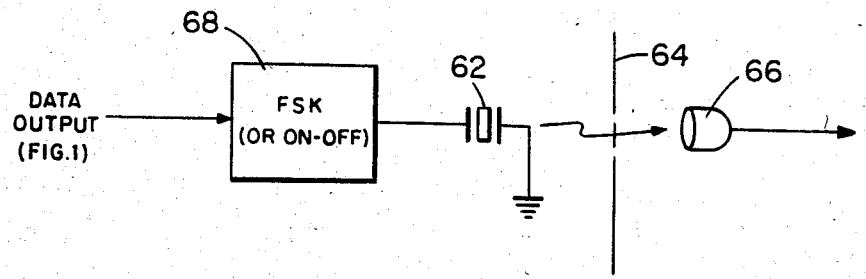
FIG. 6 is a schematic diagram of a second arrangement for transmitting data from the recording unit through the skin of the subject to demodulation circuitry.

FIG. 6 illustrates an arrangement for transmission of the digital data from the recorder 10 (either from the memory device 102 or in real time) external to the skin of the subject to the demodulator 30, and includes a frequency-shift keying (on-off) device 68, connected at its output to a piezoelectric transducer 62. A microphone 66 is located external to the skin 64 of the subject to pick up the transmitted digital signals. In operation, the FSK device 68 receives a binary data output stored in the memory device 102, or from the DATA OUT (REAL TIME) terminal, as is desired, performs frequency-shift keying thereof, and utilizes the frequency-shift keyed output to drive the piezoelectric transducer 62 for transmission of the binary data to the microphone 66, the latter being connected to conventional means for recovering the transmitted binary data and providing such binary data to the DATA INPUT terminal of external demodulator 30.

The recorder of FIG. 1 has been explained above when the MOD/DEMOD control switch 100 is in its modulate mode, i.e., wherein the shift register receives the output from comparator 16. By actuating the MOD/DEMOD switch, through the MOD/DEMOD control terminal, such that the shift register 18 receives, at its terminal D, the stored binary data from the memory device 102, the recorder 10 is converted into a demodulator to demodulate the stored binary data into an analog output (at INTEG OUT terminal) representative of the reconstructed analog ECG signal. It should be apparent that when the switch 100 is in its demodulate mode (i.e., the memory device 102 inputs into the shift register), the recorder 10 is now a demodulator identical to the external demodulator circuit as shown in FIG. 2. The demodulated analog signal, at the INTEG OUT terminal from integrator 14 can then be transmitted externally, as will be described making reference to FIG. 5.

Figure 5:
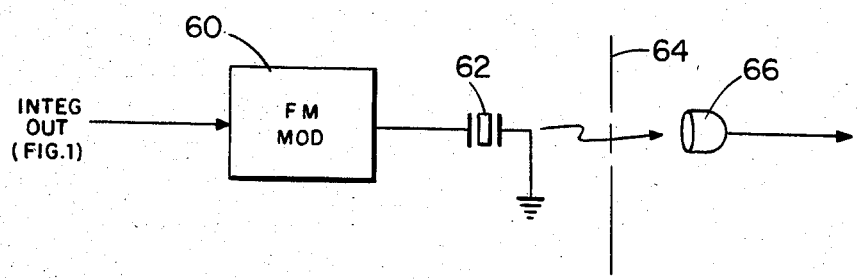
FIG. 5 is a schematic diagram of one arrangement for transmitting recorded data from the recording circuitry through the skin of the subject to demodulation circuitry.

FIG. 5 illustrates an arrangement for transmitting the demodulated analog ECG signal through the skin of the subject to detection circuitry external to the subject, the arrangement including a frequency modulator 60, piezoelectric crystal 62 and microphone 66 (located external to the skin 64 of the subject). In operation, the FM modulator 60 including an AF oscillator (not shown) located within a fully implanted device, receives the INTEG OUT output of integrator 14 (FIG. 1), performs frequency modulation, and provides the modulation output to drive the piezoelectric transducer 62, thus transmitting the analog data external to the skin 64 of the subject, where it is received by microphone 66 and can be converted (by conventional FM demodulator means) into received analog data.

To summarize, the present invention is directed to the development of a recording unit and demodulation device which employs data compression involving delta modulation. According to the technique of the present invention, the DC component of the data signal is eliminated, so that the recording device cannot transmit DC, the ECG signal staying at the DC base line. The present invention preferably operates at a rate of 200 bits-per-second, such being possible as a result of the data compression technique utilized. Moreover, as a result of the present invention, and the related data compression technique, only one-third to one-fourth of the memory is needed for a standard conversion (at a clock rate of 200 Hz.), while still obtaining high quality.

While preferred forms and arrangements have been shown in illustrating the invention, it is to be clearly understood that various changes in detail and arrangement may be made without departing from the spirit and scope of this disclosure.

What is claimed is:

1. A data recorder for recording ECG input data from within the body of a patient, comprising:
   implanted ECG input means for receiving an analog ECG waveform from the heart of the patient;
   implanted data conversion means for converting the analog ECG waveform by delta modulation into a digital pulse train which constitutes the ECG input data;
   implanted memory means for storing the digital pulse train;
   implanted transmission means for selectively transmitting the digital pulse train from the memory means across the skin of the patient to a location externally of the body of the patient, said transmission means including a piezoelectric transducer means for converting said digital pulse train into a variable audible signal for transmission across the skin of the patient to be detected externally of the body, said audible signal being representative of the originally received analog ECG waveform and varying in accordance with the characteristics of the previously stored digital pulse train.

2. The data recorder of claim 1, wherein said data conversion means comprises:
   integrator means for integrating in an upward or downward direction in response to an up/down control signal to provide an integrator output;
   comparator means for comparing the integrator output of said integrator means with said analog ECG waveform to provide a digital pulse train comprising a series of first and second output pulses, said first output pulse occurring when said integrator output is greater than the ECG waveform and said second output pulse occurring when said integrator output is less than the ECG waveform; and feedback means for feeding the digital pulse train back to said integrator means, said digital pulse train defining said up/down control signal.

3. The data recorder of claim 2, wherein said data conversion means further comprises integrator slope control means for controlling the slope of integration of said integrator means in accordance with said digital pulse train.

4. The data recorder of claim 3, wherein said integrator slope control means comprises logic means for receiving said digital pulse train and providing a logic means output signal when at least two consecutive pulses of said digital pulse train are identical, coupling means for coupling the comparator means with said logic means to provide the logic means with said digital pulse train, and means for converting said logic means output signal to an integrator slope control signal for controlling the slope of integration of said integrator means.

5. The data recorder of claim 4, wherein said coupling means comprises a shift register means for shifting and storing the digital pulse train in accordance with a clock signal, said shift register means including shift register output terminals coupled to said logic means to provide the digital pulse train to said logic means.

6. The data recorder of claim 5, wherein said logic means output signal varies in accordance with the number of consecutive identical pulses of said digital pulse train.

7. The data recorder of claim 6, wherein said means for converting the logic means output signal comprises a digital-to-analog converter means for converting the logic means output signal to an analog signal, slope control integrating means for integrating the analog signal to provide the integrator slope control signal, multiplier means having a pair of multiplier inputs, and a multiplier output, one multiplier input for receiving the integrator slope control signal the second multiplier input for receiving the up/down control signal from said feedback means, and the multiplier output coupled with said integrator means.

8. The data recorder of claim 7, wherein said memory means has a storage means input coupled with one of said shift register output terminals for receiving the digital pulse train.

9. The data recorder of claim 1, wherein said transmission means further comprises frequency-shift keying means for converting the digital pulse train to a frequency-shift keyed output signal, said frequency-shift keyed output signal coupled with said piezoelectric transducer means.

10. The data recorder of claim 1, wherein said transmission means comprises demodulation means for demodulating the digital pulse train stored in the storage means by delta demodulation to form a demodulated analog signal, and piezoelectric transducer means for converting said demodulated analog signal into an audible signal adapted to be detected externally of the body.

11. The data recorder of claim 10, wherein said transmission means further comprises FM modulation means coupled between said demodulation means and said piezoelectric transducer means for frequency modulating said demodulated analog signal.

12. The data recorder of claim 1, further comprising:

external receiving means for receiving the digital pulse train as transmitted across the skin of the patient; and external demodulation means for demodulating the received digital pulse train by delta demodulation to form an analog signal representative of the input ECG waveform.

13. The data recorder of claim 1, further comprising external receiving means for detecting said audible signal.

14. The data recorder of claim 13, further comprising external demodulation means for demodulating the received audible signal to form an analog signal representative of the ECG input waveform.

15. The data recorder of claim 14 wherein said data conversion means includes means for delta modulating the analog ECG waveform, and said demodulation means includes means for delta demodulating the received audible signal.

16. A data recorder for recording ECG input data from within the body of a patient, the recorder comprising:

implanted ECG input means for receiving an analog ECG waveform from the heart of the patient;

implanted data compression means for converting the ECG waveform by delta modulation into a digital pulse train which constitutes the ECG input data;

implanted memory means for storing the digital pulse train;

implanted demodulation means for demodulating the digital pulse train stored in said memory means by delta demodulation to form an analog signal which is a reconstruction of the received analog ECG input waveform; and implanted transmission means for selectively transmitting the analog signal from the demodulation means across the skin of the patient to a location externally of the body of the patient, said transmission means including a piezoelectric transducer means for converting said demodulated analog signal into an audible signal for transmission across the skin of the patient for detection outside the body of a patient, said audible signal being representative of the originally received analog ECG waveform and varying in accordance with the characteristics of the previously stored digital pulse train.

17. The system of claim 16, wherein said demodulation means comprises receiving means for receiving said digital pulse train from said memory means, integrator means for integrating in an upward or downward direction in response to an up/down control signal to provide an integrator output signal representative of the ECG input waveform, coupling means for coupling the digital pulse train from said receiving means to said integrator means, said digital pulse train defining the up/down control signal.

18. The system of claim 17, wherein said demodulation means further comprises integrator slope control means for controlling the slope of integration of said integrator means in accordance with said digital pulse train.

19. The system of claim 18, wherein said integrator slope control means comprises logic means for receiving said digital pulse train and providing a logic means output signal when at least two consecutive pulses of said digital pulse train are identical, said logic means receiving said digital pulse train from said receiving means, and means for converting said logic means output signal to an integrator slope control signal for controlling the slope of integration of said integrator means.

20. The data recorder of claim 19, wherein said receiving means comprises a shift register means for shifting and storing the digital pulse train in accordance with a clock signal, said shift register means including shift register output terminals coupled to said logic means to provide the digital pulse train to said logic means.

21. The system of claim 20, wherein said logic means output signal varies in accordance with the number of consecutive identical pulses of said digital pulse train.

22. The system of claim 21, wherein said means for converting the logic means output signal comprises a digital-to-analog converter means for converting the logic means output signal to an analog signal, slope control integrating means for integrating the analog signal to provide the integrator slope control signal, multiplier means having a pair of multiplier inputs and a multiplier output, one multiplier input for receiving the integrator slope control signal, the second multiplier input for receiving the up/down control signal from said coupling means, and the multiplier output coupled with said integrator means.

23. The data recorder of claim 16, wherein said data conversion means includes means for data modulating the analog ECG waveform, and said demodulation means includes means for delta demodulating the digital pulse train stored in said memory means.

24. The data recorder of claim 23, further comprising means for transferring said digital pulse train from said data conversion means to said transmission means for transmission across the skin of the patient to a location externally of the body of the patient.

* * * * *